United States Patent [19]

Lo et al.

[11] Patent Number: 4,900,659
[45] Date of Patent: Feb. 13, 1990

[54] **NUCLEOTIDE SEQUENCE COMPOSITION AND METHOD FOR DETECTION OF *NEISSERIA GONORRHOEAE* AND METHOD FOR SCREENING FOR A NUCLEOTIDE SEQUENCE THAT IS SPECIFIC FOR A GENETICALLY DISTINCT GROUP**

[75] Inventors: Andrew Lo, New York, N.Y.; Huey-Lang Yang, Tenafly, N.J.

[73] Assignee: Enzo Biochem, Inc., New York, N.Y.

[21] Appl. No.: 823,921

[22] Filed: Jan. 30, 1986

[51] Int. Cl.$^4$ ............................................. C12Q 1/68
[52] U.S. Cl. ...................................... 435/6; 435/871; 436/501; 536/27; 935/78
[58] Field of Search .................. 536/27; 436/501, 511; 935/77–79; 435/6, 871

[56] References Cited

U.S. PATENT DOCUMENTS 4,446,230  5/1984  Zubrzycki ........................... 435/871

FOREIGN PATENT DOCUMENTS 0114668  8/1984  European Pat. Off. .
0153873  9/1985  European Pat. Off. .
0173339  3/1986  European Pat. Off. .

OTHER PUBLICATIONS

C. Hoke et al. *International Journal of Systematic Bacteriology*, 32, 57–66, 1982.
B. Sorensen et al, *Journal of General Microbiology*, 131, 3099–3104, 1985.
Saunders, Chromosomal Rearrangements in Gonoccal Pathogenicity, Nature, 299:781 (1982).
Lowe, et al., Quantitation of *Neisseria gonorrhoeae* from Women with Gonorrhea, J. Inf. Dis., 133:621–626 (1976).
Odugbemi and Arco, Differentiation of *Kingella denitrificans* from *Neisseria gonorrhoeae* . . . , J. Clin Micro., 17:389–391 (1983).
Prior and Spagna, Rapid Evaluation of Gonococcal and Nongonococcal Urethritis in Men, J. Clin. Micro, 17:485–488 (1983).
Robinson and Oberhofer, Identification of Pathogenic Neisseria Species with the RapID NH, J. Clin. Micro, 17:400–404 (1983).
Bae, et al, Analysis of *Neisseria gonorrhoeae* for In Situ β-Lactamase Production . . . , J. Clin. Micro, 17:545–547 (1983).
Morello, Isolation and Identification of Neisseria, api Species, 5:1–10 (1981).

Primary Examiner—Esther M. Kepplinger
Assistant Examiner—David A. Saunders
Attorney, Agent, or Firm—Charles J. Herron; Serle I. Mosoff

[57] ABSTRACT

This invention relates to specific discrete nucleotide sequences. More precisely, this invention relates to a composition comprising discrete nucleotide sequences that are specific for *Neisseria gonorrhoeae*, as defined hereinbelow, i.e. the compositions of the subject invention can be utilized to detect *Neisseria gonorrhoeae* chromosomal DNA and thus, *Neisseria gonorrhoeae*.

6 Claims, No Drawings

NUCLEOTIDE SEQUENCE COMPOSITION AND METHOD FOR DETECTION OF *NEISSERIA GONORRHOEAE* AND METHOD FOR SCREENING FOR A NUCLEOTIDE SEQUENCE THAT IS SPECIFIC FOR A GENETICALLY DISTINCT GROUP

FIELD OF THE INVENTION

This invention relates to specific discrete nucleotide sequences. More precisely, this invention relates to a composition comprising discrete nucleotide sequences that are specific for *Neisseria gonorrhoeae*, as defined hereinbelow, i.e. the compositions of the subject invention can be utilized to detect *Neisseria gonorrhoeae* chromosomal DNA and thus, *Neisseria gonorrhoeae*.

BACKGROUND OF THE INVENTION

The persistence of *Neisseria gonorrhoeae*, one of the most prevalent bacterial diseases reported in humans, as a major health problem has resulted in the development of numerous methods for detection of *Neisseria gonorrhoeae*.

Currently accepted procedures for the determination of gonococcal infection rely primarily upon culture techniques. Typical culture techniques include procedures described in Criteria And Techniques For The Diagnosis Of Gonorrhea, published by the Center for Disease Control, Atlanta, Ga. In such culture procedures, a specimen, e.g., a urethral or cervical sample, is placed on an acceptable culture medium, e.g., Thayer-Martin medium. The cultures are incubated at 37° C. in a 5% carbon dioxide atmosphere for 24 to 48 hours. The culture plates are then inspected for the appearance of *Neisseria gonorrhoeae* colonies. Suspect colonies are gram-stained and tested for oxidase activity. Generally, presumptive diagnosis of gonococcal infection in males is determined by obtaining urethral cultures which exhibit oxidase-positive colonies of gram-negative "coffee-bean" shaped diplococci when cultured on Thayer-Martin medium. In females, gonococcal infection may be diagnosed by examining cervical cultures on Thayer-Martin medium wherein oxidase-positive colonies of gram-negative diplococci appear. Organisms from presumptively identified colonies of *Neisseria gonorrhoeae* are frequently confirmed by sugar fermentation, fluorescent antibody staining or coagglutination. However, such culture procedures are laborious, time consuming and are generally limited to the detection of "living cells". When culture methods are utilized, a specimen may be taken at one location and shipped to a laboratory, usually at another location where the organisms are cultured and identified. Thus, these culture procedures may require several days before results are obtained. Furthermore, results obtained from culture procedures may be erroneous, if, rather exacting conditions for preservation, shipment, and culturing of the bacteria are not followed.

Nucleic acid hybridization assays have been used as a tool for the detection and identification of a target genetic material such as DNA or RNA. A nucleic acid hybridization assay is premised upon the fact that the target genetic material has a specific nucleotide sequence. It is this sequence of nucleotides that is to be detected. Such detection and identification can be for a specific gene, or DNA or RNA sequence or a point mutation or deletion thereof. A number of techniques exist to carry out such assays. (See *Methods In Enzymology*, Vol. 68, R. Wu (Ed) pp. 379–469, 1979; and Dunn, A. R., and Sambrook, J., *Methods In Enzymology*, Vol. 65; Part 1, pp. 468–478, 1980). One of the most widely used procedures is called the Southern blot filter hybridization method (Southern, E., J. Mol. Biol. 98, 503, 1975). This procedure is usually used to identify a particular DNA fragment separated from a mixture of DNA fragments by electrophoretic techniques. The procedure is generally carried out by isolating a sample of DNA from some microorganism. The isolated DNA is subjected to a restriction endonuclease digestion and electrophoresed on a gel (agarose, acrylamide, etc.). When the gel containing the separated DNA fragments is blotted into a suitable matrix, eg. a nitrocellulose filter sheet or diazotized paper, the fragments are transferred and become bound to the matrix. The matrix containing the DNA fragments is then heated to denature the DNA. At this point the matrix is treated with a solution containing a denatured labelled polynucleotide probe and hybridization is allowed to take place. The labelled polynucleotide probe is a nucleotide sequence that is complementary to the DNA fragment that is desired to be detected and which has attached thereto a detectable marker. The detectable marker permits one to verify that the polynucleotide probe has hybridized to the DNA fragment that is desired to be detected. Numerous techniques for labelling a polynucleotide probe with a detectable marker are known. For example, see European Patent Applications publication numbers 0 063 873 and 0 097 373, the disclosures of which are incorporated herein by reference. The unhybridized labelled polynucleotide probe is then separated from the labelled polynucleotide probe that has hybridized to the DNA fragment that is desired to be detected. Separation is generally carried out by washing. The detectable marker of the DNA probe is then detected.

It would be useful to have a polynucleotide probe for the detection of *Neisseria gonorrhoeae*. A nucleotide sequence derived from the gonococcal cryptic plasmid has been utilized as a polynucleotide probe to detect *Neisseria gonorrhoeae*. However, such a polynucleotide probe, at best, can only detect those strains of *Neisseria gonorrhoeae* that contain plasmid DNA. It is believed that from about 40% to about 96%, depending on geographic location, of the strains of *Neisseria gonorrhoeae* contain plasmid DNA. Since such a polynucleotide probe can only detect those strains of *Neisseria gonorrhoeae* that contain plasmid DNA, such a polynucleotide probe is of limited utility internationally. See DNA Hybridization Technique for the Detection of *Neisseria gonorrhoeae* in men with Urethritis, THE JOURNAL OF INFECTIOUS DISEASES, VOL. 148, NO. 3, pages 462–471, September 1983. Therefore, it would be preferred to utilize a nucleotide sequence as a polynucleotide probe that is capable of hybridizing to *Neisseria gonorrhoeae* chromosomal DNA.

There is an extremely high degree of DNA homology between the chromosomal DNA of *Neisseria gonorrhoeae* and *Neisseria meningitidis*, both of which are species of the genus Neisseria. It has been reported that one strain of *Neisseria gonorrhoeae* and one strain of *Neisseria meningitidis* have anywhere from about 80% to about 93% chromosomal DNA homology. See Deoxyribonucleic Acid Homologies Amount Species of the Genus Neisseria, Journal of Bacteriology, Vol. 94, No. 4, October 1967, pp. 870–874 and Taxonomy of the Neisseriae; Deoxyribonucleic Acid Base Composition, Interspecific Transformation, and Deoxyribonucleic Acid Hybridization, International Journal of Systematic Bacteriology, Vol. 32, No. 1, January 1982, pp. 57-66. This is an enormously high level of DNA homology, especially in view of the fact that organisms with as little as 70% DNA homology can be considered to be within the same subspecies. See Bergey's Manual of Systematic Bacteriology, Vol. 1, p. 11, published by Williams and Wilkins (1984).

Even further, it is believed that there is an even higher degree of DNA homology between any one strain of *Neisseria gonorrhoeae* and the sum total of numerous strains of *N. meningitidis*. This is due to that the portion of the genome of *Neisseria gonorrhoeae* that is homologous to the chromosomal DNA of each strain of *Neisseria meningitidis* may not be identical. Consequently, an even smaller percentage, if any, of the *Neisseria gonorrhoeae* genome is nonhomologous to the sum total of numerous strains of *Neisseria meningtidis*. A further technical problem is that the portion of the chromosomal *Neisseria gonorrhoeae* DNA that is nonhomologous to the sum total of numerous strains of *Neisseria meningitidis*, if any, may not exist as a discrete nucleotide sequence or sequences, but rather, as nucleotide sequences of only a few nucleotides dispersed throughout the *Neisseria gonorrhoeae* genome. For the purpose of the present invention, a "discrete nucleotide sequence" is a nucleotide sequence greater than about 12 nucleotides.

Moreover, even if a discrete nucleotide sequence of *Neisseria gonorrhoeae* were to exist that is specific for the strain of *Neisseria gonorrhoeae* from which it is derived, in order for such sequence to be useful as a polynucleotide probe it is essential that it be specific for other strains of *Neisseria gonorrhoeae* as well. Otherwise, as with the polynucleotide probe derived from the gonococcal cryptic plasmid, such nucleotide sequence by itself would be of very limited utility.

It should be noted that the genome of any strain of *Neisseria gonorrhoeae* and *Neisseria meningitidis* is each about 3 million nucleotides. A skilled scientist can sequence about 2,000 nucleotides per month. Thus, it would take 3,000 scientists one month to sequence the genome of one strain of *Neisseria gonorrhoeae* and one strain of *Neisseria meningitidis*.

SUMMARY OF THE INVETION

It is an object of subject invention to provide a composition that comprises discrete nucleotide sequences that are specific for *Neisseria gonorrhoeae* chromosomal DNA, as defined hereinbelow.

It is another object of the subject invention to provide a method for obtaining the discrete nucleotide sequences that are specific for a genetically distinct group.

The subject invention provides a composition of matter that is specific for *Neisseria gonorrhoeae* comprising at least one discrete nucleotide sequence wherein said composition gives a ratio of the lowest of the average amount of said composition hybridized to purified chromosomal DNA of the following six strains of *Neisseria gonorhoeae*:

(1) ATCC 53420
(2) ATCC 53421
(3) ATCC 53422
(4) ATCC 53423
(5) ATCC 53424
(6) ATCC 53425, normalized to equal amounts of said purified chromosomal DNA of said six strains of *Neisseria gonorrhoeae*, to the highest of the average amount said composition hybridized to purified chromosomal DNA of the following six strains of *Neisseria meningitidis*:

(1) ATCC 53414
(2) ATCC 53415
(3) ATCC 53416
(4) ATCC 53417
(5) ATCC 53418
(6) ATCC 53419, normalized to equal amounts of said purified chromosomal DNA of said six strains of *Neisseria meningitidis*, greater than about five.

The subject invention invention also provides a method for screening a nucleotide sequence that is specific for a genetically distinct group which comprises:

a. forming a separate test dot on a matrix for each sample that said nucleotide sequence is to be screened against wherein each test dot comprises purified DNA in single stranded form from one of said samples;

b. contacting said test dots with said nucleotide sequence wherein said nucleotide sequence is a single stranded nucleotide sequence insert in a bacteriophage DNA wherein said bacteriophage is a bacteriophage that has a single-stranded DNA stage in its life cycle, under hybridizing conditions;

c. separating said nucleotide sequence that did not hybridize to said test dots from said nucleotide sequence that did hybridize to said test dots;

d. contacting said test dots with denatured double stranded DNA of said bacteriophage wherein said denatured double-stranded DNA of said bacteriophage has a detectable marker attached thereto, under hybridizing conditions;

e. separating said double-stranded DNA of said bacteriophage that did hybridize to said test dots from said double-stranded DNA of said bacteriophage that did not hybridize to said test dots; and f. detecting said nucleotide sequence by means of said detectable marker.

DETAILED DESCRIPTION OF THE INVENTION

The method of identifying the discrete nucleotide sequences of the compositions of the subject invention, which are specific for *Neisseria gonorrhoeae* chromosomal DNA, as defined hereinbelow, can be carried out by virtually any screening technique. One such technique is commonly referred to as colony hybridization. See M. Grunstein et al., "Colony hybridization; A method for the isolation of cloned DNAs that contain a specific gene", Proceedings National Academy of Science, Vol. 72, p 3961 (1975). Another such technique is commonly referred to as plaque hybridization. See Benton et al., "Screening lamda gt recombinant clones by hybridization to single plaques in situ", Science, Vol. 196, p 180 (1977); Woo, "A sensitive and rapid method for recombinant phage screening", Methods in Enzymology, Vol. 68, p 389 (1979); and Woo et al., "The ovalbumin gene: Cloning of the natural gene", Proceedings National Academy of Science, Vol. 75, p 3688 (1978). Also, an excellent text that discloses screening techniques in detail is Molecular Cloning, Maniatis et al., published by Cold Spring Harbor Laboratory.

The method of the subject invention utilizes the following steps:

A. Purification and Digestion of Plasmid-Free *Neisseria gonorrhoeae* chromosomal DNA.
B. Formation of a Recombinant Molecule.
C. Transformation of the Recombinant Molecule.
D. Screening of Host Cells.
E. Amplification of the Recombinant Molecule.
F. The Screening Procedure.
G. Detection of Recombinant Bacteriophage DNA/Test Dot Complex.
H. Identification of those Recombinant Bacteriophage Containing Discrete Nucleotide Sequences that are specific for *Neisseria gonorrhoeae* chromosomal DNA.

Each of the steps can be carried out as follows:

A. Purification and Digestion of Plasmid-Free *Neisseria Gonorrhoeae* Chromosomal DNA In order to isolate discrete nucleotide sequences that are specific for *Neisseria gonorrhoeae* chromosomal DNA, the chromosomal DNA must be separated from the rest of the cell. This can be carried out by taking any strain *Neisseria gonorrhoeae* and placing it on an appropriate agar plate, e.g., Thayer-Martin or chocolate agar, and permitting the strain to proliferate by incubating in an atmosphere containing 5% $CO_2$. After growth for about 16–18 hours the cells are collected into a test tube and the cells are lysed with a lysing agent, eg. a detergent. A preferred detergent is sodium dodecyl sulfate (SDS). This results in the *Neisseria gonorrhoeae* chromosomal DNA being accessible so that it can be purified from its cellular debris.

The *Neisseria gonorrhoeae* chromosomal DNA is then purified from its cellular debris. This can be carried out by standard techniques, for example, phenol extraction followed by alcohol precipitation and centrifugation to equalibrium in a cesium chloride-ethidium bromide density gradient.

It is preferred that the strain of *Neisseria gonorrhoeae* utilized contains no plasmids, including cryptic plasmid. If a strain of *Neisseria gonorrhoeae* containing a plasmid is utilized, it is essential to first remove such plasmids and then isolate the *Neisseria gonorrhoeae* chromosomal DNA. The removal of the plasmid can be carried out by centrifugation to equilibrium in cesium chloride-ethidium bromide gradient or in a sucrose gradient, or by agarose gel electrophoresis.

The purified plasmid-free *Neisseria gonorrhoeae* chromosomal DNA is now digested into fragments. This can be carried out by utilizing any restriction enzyme that can digest *Neisseria gonorrhoeae* chromosomal DNA. Suitable restriction enzymes that can be utilized for such purpose include MboI, Taq I and Hind III. However, it is preferred to utilize an enzyme that recognizes only four bases, such as Mbo I. It is preferred to utilize an enzyme that recognizes only four bases because this will result in DNA fragments containing fewer base pairs. In view of the high degree of homology between the *Neisseria gonorrhoeae* chromosomal DNA and *Neisseria meningitidis* DNA, the smaller the DNA fragment, the less likely the DNA fragment will contain a nucleotide sequence that is capable of hybridizing to *Neisseria meningitidis.* Theoretically, Mbo I digestion produces, on average, DNA fragments containing about 256 base pairs. It should be noted that it is essential that the DNA fragments be greater than about 12 nucleotides. A DNA fragment containing fewer than about 12 nucleotides does not have sufficient complexity to be specific for a given organism.

To verify that the digestion has proceeded sufficiently for cloning into the appropriate vector, as discussed hereinbelow, agarose gel electrophoretic techniques can be utilized to measure the size of the DNA fragments.

B. Formation of a Recombinant Molecule

Each of the *Neisseria gonorrhoeae* chromosomal DNA fragments now can be inserted into a vector to form a recombinant molecule. For the screening procedure of the subject invention it is essential to utilize a bacteriophage DNA as the vector and further, a bacteriophage which has a single-stranded DNA stage in its life cycle.

A bacteriophage provides the advantage that upon proliferation of bacteria that are infected with a bacteriophage, the bacteriophage is extruded from the bacteria. Thus, the bacteriophage can be easily purified from the host bacteria. Purified DNA is essential for the DNA to be labelled efficiently, and for the DNA to hybridize to its target DNA effectively. Furthermore, the cellular debris, which is present in unpurified DNA, can cause nonspecific binding. Nonspecific binding results in a false signal. Also, since the bacteriophage is extruded from the bacteria, nature essentially purifies the bacteriophage from the bacteria which otherwise would be prohibitively time consuming.

The use of a bacteriophage that has a single stranded DNA stage in its life cycle provides the advantage that hybridization with single-stranded DNA eliminates the possibility that such DNA can anneal to itself rather than to the target DNA. Thus, a greater percentage of the single-stranded DNA can hybridize to the target DNA which results in increased sensitivity. Suitable bacteriophage include the fl bacteriophage, fd bacteriophage, M13 bacteriophage and their derivatives e.g. the mp series of the M13 bacteriophage.

To construct the recombinant molecule, the double-stranded replicative form (RF) of the bacteriophage, DNA, which is circular, is linearized. This is carried out with the appropriate restriction enzyme. The choice of restriction enzyme should be such that the *Neisseria gonorrhoeae* chromosomal DNA fragment can be ligated into the linearized RF bacteriophage DNA. This ligation can be carried out by blunt end ligation or cohesive end ligation, both of which are standard techniques. See Molecular Cloning, Maniatis et al., published by Cold Spring Harbor Laboratory. It is preferred to insert the MboI *Neisseria gonorrhoeae* chromosomal DNA fragment into the Bam HI site of a M13mp vector.

C. Transformation of the Recombinant Molecule

Transformation of the recombinant molecule into a suitable host cell now can be carried out. Although it is believed that any host cell can be utilized, it is preferred that the host cell be a male *E. coli.* Male *E. coli* is preferred because the vectors of the present invention that are utilized to make the recombinant molecule are derived from male specific bacteriophage. Thus, upon amplification by growing the recombinant bacteriophage in the male *E. coli,* as described hereinbelow, the bacteriophage produced can reinfect the male *E. coli* and thus, retard the growth of the male *E. coli,* resulting in the formation of a plaque. A plaque is visually identifiable. Therefore, one can easily select from the lawn of male *E. coli* those male *E. coli* that have been transformed.

It is preferred that the male *E. coli* be selected from the group consisting of male *E. coli* that permit one to readily distinguish those plaques that contain the recombinant molecule from those plaques that contain vector alone, for example JM 103 and JM 105. The plaques on a Isopropyl-B-D-thio-galactopyranoside plate produced by JM 103 and JM 105 are white if the recombinant molecule is present and blue if the vector alone is present, assuming that the M-13 bacteriophage is utilized.

There several procedures by which transformation can be carried out. For example, transformation can be carried out by the calcium chloride procedure or the calcium chloride/rubidium chloride procedure. These procedures are standard techniques. See Maniatis.

D. Screening of Host Cells

The screening of the host cells determine those host cells that have been transformed from those that have not can now be carried out. Such screening procedure can be carried out by any standard technique. A preferred technique is as follows:

Prepare the following reagents fresh prior to use.
1. IPTG (100 mM) IPTG is Isopropyl-B-D-thio-galactopyranoside, 100 mM in $H_2O$.
2. X-gal (2% in dimethylformamide), X-GAL is 5-bromo-4-chloro-3-indolyl-B-galactoside.
3. Prepare a fresh 200 ul batch of the host cell.

The IPTG, X-gal and host cell can be prepared in batch. The X-gal and IPTG should be freshly prepared and kept on ice. It is preferred to prepare the host cell by adding a drop of overnight host cell culture to 20 ml fresh 2 x TY (per liter 16 g bacto tryptone, 10 g yeast extract, 5 g NaCl).

Add 270 ul of host cells/X-gal/IPTG mix to a tube of the transformant cells. Add 3 ml molten H top agar (per liter 10 g bacto tryptone, 8 g NaCl, 8 g agar), kept at 42° C. Mix by rolling, and pour immediately onto a prewarmed (37° C.) H plate (per liter 10 g bacto tryptone, 8 g NaCl, 12 g agar). Leave at room temperature to set. Invert the plates. Incubate at 37° C. overnight.

After overnight growth, i.e. growth for about 12 hours to about 18 hours, transformed cells will have formed plaques which, in the case of male *E. coli*, are areas of retarded growth. It should now be determined which plaques contain the recombinant molecule.

This determination can be readily determined if the host cell is one that itself permits one to visually distinguish those plaques that contain the recombinant molecule from those that contain the vector along, eg. JM 103 and JM 105. If the host cell does not permit one to readily visually make this determination, such determination can be made by screening the plaques by hybridization (See Maniatis) utilizing a $^{32}P$ labelled *Neisseria gonorrhoeae* genomic DNA as a probe. This probe should be derived from the same *Neisseria gonorrhoeae* strain that is being utilized for cloning.

E. Amplification of the Recombinant Molecule

Amplification of the recombinant molecule in the host cell now can be carried out. The role of amplification is to increase the number of recombinant molecules and can be carried out by any standard techniques. A preferred technique is as follows:

The plaques containing the recombinant molecule can now be picked and inoculated in a container, eg. an Eppendorf tube, that contains host cells. The container is incubated at 37° C. with shaking overnight. This incubation results in the proliferation of the bacteriophage. During incubation the mature bacteriophage is extruded from the host cell. Centrifugation can be employed to separate the extruded bacteriophage from the host cells. The supernatant contains the bacteriophage and is utilized for screening, as described hereinbelow.

F. The Screening Procedure

The extruded bacteriophage now can be utilized for screening. The extruded bacteriophage are screened against test dots. A test dot is denatured purified chromosomal DNA bound to a suitable matrix.

Each of the test dots consists of denatured purified chromosomal DNA isolated from one of the following strains of *Neisseria gonorrhoeae* and *Neisseria meningitidis* which are listed by their American Type Culture Collection (ATCC) accession number, each of which was deposited on Jan. 8, 1986. The ATCC is located at 12301 Parklawn Drive, Rockville, Md. 20852.

| *Neisseria meningitidis* | *Neisseria gonorrhoeae* |
|---|---|
| 1. 53414 | 1. 53420 |
| 2. 53415 | 2. 53421 |
| 3. 53416 | 3. 53422 |
| 4. 53417 | 4. 53423 |
| 5. 53418 | 5. 53424 |
| 6. 53419 | 6. 53425 |

The tests dots can be prepared as follows:

The ATCC supplies the sample of the strain in a lypholized state. The sample is grown in the appropriate medium to amplify the number of bacterial cells. The chromosomal DNA is then isolated from the bacterial cells by standard techniques such as by utilizing a detergent, e.g. SDS, to lyse the cell, RNase to digest the RNA and then phenol extraction to purify the chromosomal DNA. The purified chromosomal DNA is denatured with alkali, e.g. NaOH, or heat. The denatured purified chromosomal DNA is adjusted to have a pH from about 7.8 to about 8.0 by adding 1M NH4Ac-0.02N NaOH. See Nucleic Acid Research, Vol. 7, p. 1541 (1979) Kafatos et al. The solution is then dotted onto a suitable matrix, e.g. a nitrocellulose filter. Thus, the chromosomal DNA is bound to the matrix in single stranded form, and this constitutes the test dot. Each test dot should contain about 1.0 ug of the denatured purified chromosomal DNA. Each of the 12 test dots is situated on the same matrix.

The test dots now can be fixed to the matrix and blocked. Fixing is carried out to stabilize the test dots to prevent the denatured purified chromosomal DNA from being washed off the matrix during the subsequent hybridization/wash step and blocking is carried out to prevent any non-specific binding to the matrix by the recombinant bacteriophage DNA and the labelled probe. Fixing can be carried out by placing the matrix under vacuum at 80° C. for about two hours. Blocking can be carried by incubating the matrix, in any standard hybridization solution, eg. 2X SSC, 5X Denhardt's solution, 0.1% SDS, and 200 ug/ml. of sonicated heat-denatured calf thymus DNA, at about 65° C. for at least about two hours. The hybridizaiton solution is discarded and the matrix containing the test dots is ready to be screened with the recombinant bacteriophages.

The matrix is then placed in fresh hybridization solution consisting of 2XSSC, 5X Denhardt's solution and 0.1% SDS, and 200 ug/ml. of sonicated heat denatured calf thymus DNA to which is added the supernatant, which contains the recombinant bacteriophage. The *Neisseria gonorrhoeae* insert in the recombinant bacteriophage DNA can now hybridize to the test dots by permitting the bacteriophage DNA to remain in contact with the matrix at 65° C. for about 16 to about 20 hours. It should be noted that hybridization at 65° C. also destroys the protein coat of the recombinant bacteriophage DNA. Then, the hybridization solution is removed and the matrix washed twice for about 30 minutes each in 2X SSC, 0.1% SDS followed by two more 30 minute washes in 0.2X SSC, 0.1% SDS, all at 65° C., with gentle shaking during each of the four washes.

It should be noted that to screen each recombinant bacteriophage, each recombinant bacteriophage must be separately screened against a suitable matrix containing the twelve test dots.

It should also be noted that rather than screening the recombinant bacteriophage against each of the six strains of *Neisseria gonorrhoeae* and six strains of *Neisseria meningitidis*, one can screen against only one of the strains of *Neisseria gonorrhoeae* and one of the strains of *Neisseria meningitidis*. This is because substantially all of the recombinant bacteriophage that hybridize to the DNA of one strain of each of these Neisseria species will also hybridize to the other listed strains of each of these species. Those recombinant bacteriophage that do not, will be eliminated in step H. The screening of only one strain of each of these species permits one to carry out the screening procedure in significantly less time.

G. Detection of Recombinant Bacteriophage Dot Complex DNA/Test

Each of the recombinant bacteriophage DNA/test dot complexes now can be detected. This detection can be carried out by utilizing the double stranded replicative form (RF) of the parent bacteriophage as a labeled probe. This RF DNA is capable of hybridizing to the vector portion of the recombinant bacteriophage DNA/test dot complex to form a bridge consisting of the RF DNA hybridized to the recombinant bacteriophage DNA which is hybridized to the test dot. The bridge is then detected by means of the label of the RF DNA.

This method of detection of the complex provides numerous benefits. First, this method only requires one labelling step, the labelling of the RF DNA. This labelled RF DNA can be utilized to detect all of the recombinant bacteriophage. Otherwise, each recombinant bacteriophage must be separately labelled, an extremely time consuming and labor intensive procedure. Second, even further, by this method of detection one can detect all of the recombinant bacteriophage DNA/test dot complexes simultaneously. This saves much time during the detection step. Finally, this method of detection provides increased sensitivity as compared to if the recombinant bacteriophage were to be labelled. This is due to the fact that the nick translation reaction chops a vector into many DNA fragments. Therefore, if the recombinant bacteriophage were to be labelled by nick translation, only those DNA fragments containing the *Neisseria gonorrhoeae* would contribute to the signal. However, if the RF DNA is labelled by nick translation, all of the resulting DNA fragments can hybridize to the vector portion of the recombinant bacteriophage thus providing increased sensitivity.

The RF DNA of the parent bacteriophage is labelled with $^{32}P$ by, eg. nick translation, and utilized as a probe to detect the recombinant bacteriophage/test dot complex. The preparation of the $^{32}P$ labelled RF DNA can be prepared by standard techniques. See Rigby et al., Journal Molecular Biology (1977), 113, pp. 237-251. The $^{32}P$ labelled RF DNA now can be utilized to detect the recombinant bacteriophage/test dot complex. This can be carried out as follows:

The $^{32}P$ labelled RF DNA is denatured by, for example, boiling it in water. The denatured $^{32}P$ labelled RF DNA is added to a hybridization solution consisting of 2X SSC, 5X Denhardt's solution and 0.1% SDS, and 200 ug./ml. of sonicated heat-denatured calf thymus DNA to form a mixture which is then placed in contact with the matrix containing the recombinant bacteriophage DNA/test dot complex for about 12–16 hours at 65° C. This results in the $^{32}P$ labelled RF DNA hybridizing to the vector portion of the recombinant bacteriophage DNA/test dot complex to form a $^{32}P$ labelled RF DNA/recombinant bacteriophage DNA/test dot bridge. The matrix is then washed twice for about 30 minutes each in 2XSSC, 0.1% SDS followed by two more 30 minutes washes in 0.2X SSC 0.1% SDS, all at 65° C., with gentle shaking during each of the four washes. The matrix is then air dried.

The radioactivity of the $^{32}P$ of the bridge is now quantified. This can be carried out by exposing the matrix to X-ray film. The X-ray film is used as a reference marker by placing it over the matrix utilizing $^{32}P$ dye marker as reference points to allign the signal dots on the film with the corresponding test dots, thus one can locate the test dots on the matrix. Each test dot is then cut out from the matrix and placed in a vial containing scintillation fluid.

The vial is then placed in a scintillation counter and the radioactivity of the bridge is quantified. After subtracting matrix background, the number of counts per minute of each of the *Neisseria gonorrhoeae* test dots and each of the *Neisseria meningitidis* test dots for each recombinant bacteriophage DNA is then calculated. For each recombinant bacteriophage DNA, the number of counts per minutes of the strain of *Neisseria gonorrhoeae* with the fewest number of counts per minute, is compared to the number of counts per minute of the strain of *Neisseria meningitidis* with the greatest number of counts per minute and those recombinant bacteriophage DNAs that give a ratio, based upon number counts per minute, of *Neisseria gonorrhoeae*: *Neisseria meningitidis* greater than about five are utilized in the following procedure.

H. Identification of those Recombinant Bacteriophage Containing Discrete Nucleotide Sequences that are Specific for *Neisseria Gonorrhoeae* Chromosomal DNA Those recombinant bacteriophage that give such a ratio of *Neisseria gonorrhoeae*: *Neisseria meningitidis* greater than about five, are then further analysed. This further analysis utilizes the direct labelling of the RF DNA of these recombinant bacteriophage. The direct labelling of the RF DNA of these recombinant bacteriophage permits one to more precisely quantify the ratio described hereinabove of *Neisseria gonorrhoeae*: *Neisseria meningitidis* and thus allows one to precisely identify those recombinant bacteriophage that contain discrete nucleotide sequences that are specific for *Neisseria gonorrhoeae* chromosomal DNA and thus define the compositions of the subject invention.

This further analysis can be performed as follows:

Aliquots of each of the recombinant bacteriophage that give such a ratio of *Neisseria gonorrhoeae: Neisseria meningitidis* greater than about five are inoculated into growth media, eg. 2X TY medium or LB medium, together with uninfected host cells and are allowed to grow for about five hours at 37° C. This results in the amplification of the recombinant bacteriophage. The now infected host cells are centrifuged and the RF DNA, which contains a *Neisseria gonorrhoeae* chromosomal DNA fragment, is isolated by standard techniques. See Maniatis. A 100 ml. culture should yield about 40–50 ug of RF DNA.

The RF DNA is now labelled with $^{32}P$ by, for example, nick translation. The $^{32}P$ labelled RF DNA is then utilized as a probe to screen against test dots comprising the following denatured purified chromosomal DNA, which is derived from the same strains of *Neisseria gonorrhoeae* and *Neisseria meningitidis* as utilized hereinabove, listed by their ATCC accession number:

| *Neisseria meningitidis* | *Neisseria gonorrhoeae* |
|---|---|
| 1. 53414 | 1. 53420 |
| 2. 53415 | 2. 53421 |
| 3. 53416 | 3. 53422 |
| 4. 53417 | 4. 53423 |
| 5. 53418 | 5. 53424 |
| 6. 53419 | 6. 53425 |

The test dots are prepared as described hereinabove. But, each strain of *Neisseria gonorrhoeae* and *Neisseria meningitidis* should have six test dots with each test dot for each strain being serially diluted by a factor of 10 such that the six test dots contain the following amounts of denatured purified chromosomal DNA: 500 nanograms, 50 nanograms, 5 nanograms, 0.5 nanograms, 50 picograms and 5 picograms. Thus, there will be six test dots for each strain resulting in a total of 72 test dots for each recombinant bacteriophage to be screened against. It is preferred that all 72 test dots be on the same matrix so that when the hybridization is carried out with the $^{32}P$ labelled RF DNA, such DNA will hybridize to the test dots under identical conditions.

The $^{32}P$ labelled RF DNA is now utilized to hybridize to the test dots. This can be carried out as follows:

The $^{32}P$ labelled RF DNA is denatured by, for example, boiling it in water. The denatured $^{32}P$ labelled RF DNA is added to a hybridization solution consisting of 2X SSC, 5X Denhardt's solution and 0.1% SDS, and 200 ug./ml. of sonicated heat-denatured calf thymus DNA to form a mixture which is then placed in contact with the matrix containing the test dots for about 12–16 hours at 65° C. This results in the $^{32}P$ labelled RF DNA hybridizing to the test dot, if the test dot contains DNA sequences substantially complementary to the *Neisseria gonorrhoeae* chromosomal DNA fragment contained in the $^{32}P$ labelled RF DNA, to form a hybrid. The matrix is then washed twice for about 30 minutes each in 2X SSC, 0.1% SDS followed by two more 30 minutes washes in 0.2X SSC, 0.1% SDS, all at 65° C., with gentle shaking during each of the four washes. The matrix is then air dried. It is essential that such hybridization and washes be carried out at the stated temperature and salt concentrations.

The radioactivity of the $^{32}P$ of the hybrid is now quantified. This can be carried out by exposing the matrix to X-ray film. The X-ray film is used as a reference marker by placing it over the matrix utilizing 32P dye marker as reference points to allign the signal dots on the film with the corresponding test dots. Each test dot is then cut out from the matrix and placed in a vial containing scintillation fluid.

The vial is then placed in a scintillation counter and the radioactivity of the $^{32}P$ of the hybrid is quantified. For each recombinant bacteriophage DNA, the number of counts per minute of each of the *Neisseria gonorrhoeae* test dots and each of the *Neisseria meningitidis* test dots is then calculated and compared.

The calculation is carried out as follows: After subtracting matrix background, for each of the six test dots of each strain of *Neisseria gonorrhoeae* and *Neisseria meningitidis* calculate the number of counts per minute with 500 nanograms of purified chromosomal DNA of the test dots, i.e., the amount of *Neisseria gonorrhoeae* DNA hybridized to a test dot normalized to equal amounts (500 nanograms) of purified chromosomal DNA of the test dot. Of course, values other than 500 nanograms can be utilized; it is only essential that the counts per minute be normalized. Then take two of such numbers for each of the six test dots of each of the strains of *Neisseria gonorrhoeae* and *Neisseria meningitidis* that are: (1) most nearly the same, thus most close to a linear relationship, and (2) the amount of the purified chromosomal DNA of such test dots differs by a factor of 10 and calculate their average, i.e., the average amount of *Neisseria gonorrhoeae* DNA hybridized to the purified chromosomal DNA of a given strain of *Neisseria gonorrhoeae* or *Neisseria meningitidis* normalized to equal amounts of purified chromosomal DNA of that given strain of *Neisseria gonorrhoeae* or *Neisseria meningitidis*. For each recombinant bacteriophage DNA, take the lowest of the average amount of *Neisseria gonorrhoeae* DNA hybridized to the purified chromosomal DNA of each of the six strains of *Neisseria gonorrhoeae* normalized to equal amounts of purified chromosomal DNA of each of the six strains of *Neisseria gonorrhoeae* and the highest average amount of *Neisseria gonorrhoeae* DNA hybridized to the purified chromosomal DNA of each of the six strain of *Neisseria meningitidis* normalized to equal amounts of purified chromosomal DNA of each of the six strains of *Neisseria meningitidis* and calculate the ratio of such lowest average to such highest average.

Those compositions that comprise discrete nucleotide sequences that give such a ratio of *Neisseria gonorrhoeae: Neisseria meningitidis* greater than about five define those compositions comprising discrete nucleotide sequences that are specific for *Neisseria gonorrhoeae* chromosomal DNA, and therefore, *Neisseeria gonorrhoeae* and, thus make up the compositions of the subject invention. For the purpose of the subject invention, a "discrete nucleotide sequence" means a nucleotide sequence greater than about 12 nucleotides. In a preferred embodiment, the compositions of subject invention comprise of those discrete nucleotide sequences that give such a ratio of *Neisseria gonorrhoeae: Neisseria meningitidis* greater than about 25 and more preferrably greater than about 50. It is believed that if a discrete nucleotide sequence gives such a ratio of *Neisseria gonorrhoeae: Neisseria meningitidis* greater than about five, then such discrete nucleotide sequence will hybridize to virtually all strains of *Neisseria gonorrhoeae* and to no strain of *Neisseria meningitidis*.

The compositions of the subject invention can contain components other than discrete nucleotide sequences that are specific for *Neisseria gonorrhoeae*, eg. non Neisseria DNA, cellular debris, so long as such components do not render the compositions of the subject invention ineffective. Also, of course, the discrete nucleotide sequences of the subject invention can, as part the discrete nucleotide sequence, contain other nucleotide sequences that are irrelevent, eg. nucleotide sequences of a vector or nucleotide sequences that are a tail that is for example, enzymatically labeled.

Three discrete nucleotide sequences that give such a ratio of *Neisseria gonorrhoeae: Neisseria meningitidis* that is greater than about 50 were deposited in the ATCC on Jan. 9, 1986 and were given the ATCC acession numbers 53409, 53410 and 53411. These discrete nucleotide sequences were identified after screening about 3,000 recombinant bacteriophage that were derived from a clinical sample of *Neisseria gonorrhoeae*, which had been digested with the restriction enzyme MboI, by the method described hereinabove, wherein the vector utilized was the M13 mp8 vector and the host cell utilized was *E. coli* JM103. These three discrete nucleotide sequences were further tested against about 20 strains of *Neisseria gonorrhoeae* and 10 strains of *Neisseria meningitidis* and each of the three discrete nucleotide sequences hybridized to the chromosomal DNA of the 20 strains of *Neisseria gonorrhoeae* and not to the chromosomal DNA of the 10 strains *Neisseria meningitidis.*

These three discrete nucleotide sequences were deposited in the form of a recombinant DNA molecule separately inserted at the Bam Hl site of the M13 mp 8 vector, which recombinant molecule has been transformed into the bacterial host *E. coli* JM103. The discrete nucleotide sequence insert can be isolated, if desired, from the M13 mp 8 vector by utilizing the appropriate restriction enzyme. The restriction enzyme Sau 3A can be utilized to isolate the discrete nucleotide sequence insert.

This enzyme digests the M13 mp 8 vector into seven DNA fragments of the following size: 4,014 bp., 1,696 bp., 507 bp., 434 bp., 332 bp., 149 bp. and 96 bp. and also cuts out the insert as one discrete nucleotide sequence which contains no portion of the vector. As an alternative the restriction enzymes EcoRI and Sal I can be utilized in combination to digest the vector. This digestion results in only two fragments, one being about 8 kb. and the other would contain the discrete nucleotide sequence insert and in addition about 20 bp. of the vector DNA. The discrete nucleotide sequence insert of ATCC 53409 and ATCC 53411 is each about 850 bp. and of ATCC 53410 is about 1,300 bp. After digestion with the appropriate restriction enzyme, the discrete nucleotide sequence insert can be isolated by utilizing gel electrophoretic techniques which separates the DNA fragments by size. It should be noted that by utilizing the restriction enzymes EcoRI and Sal I it is easier to isolate the discrete nucleotide sequence insert because the digestion will result in only two DNA fragments. Also, the DNA fragment containing the discrete nucleotide sequence insert will contain about 20 bp. of the vector, albeit such 20 bp. does not interfere with the specificity of the discrete nucleotide sequence insert.

The subject invention also includes the discrete flanking nucleotide sequences that are specific for *Neisseria gonorrhoeae* of the deposited discrete nucleotide sequences that are specific for *Neisseria gonorrhoeae.* For the purpose of the present invention, flanking nucleotide sequences of the deposited discrete nucleotide sequences that are specific for *Neisseria gonorrhoeae* are the nucleotide sequences of the *Neisseria gonorrhoeae* chromosomal DNA of all of the six deposited strains of *Neisseria gonorrhoeae* directly adjacent to the discrete nucleotide sequence or sequences that the deposited discrete nucleotide sequences that are specific for *Neisseria gonorrhoeae* hybridize to. It is likely that at least a portion of the flanking nucleotide sequences are specific for *Neisseria gonorrhoeae.* The discrete flanking nucleotide sequences that are specific for *Neisseria gonorrhoeae* can be obtained by the procedure described in Example I.

Also included within the subject invention are discrete subsequences of the deposited discrete nucleotide sequences that are specific for *Neisseria gonorrhoeae* and subsequences of discrete flanking nucleotide sequences that are specific for *Neisseria gonorrhoeae,* as defined hereinabove. Such discrete subsequences are capable of hybridizing to the deposited discrete nucleotide sequences.

Also included within the subject invention are discrete nucleotide sequences that are derived from mutational changes of the deposited discrete nucleotide sequences that are specific for *Neisseria gonorrhoeae,* discrete flanking nucleotide sequence thereof that are specific for *Neisseria gonorrhoeae* and subsequences thereof that are specific for *Neisseria gonorrhoeae,* if such mutated discrete nucleotide sequences are specific for *Neisseria gonorrhoeae,* as defined hereinabove.

The subject invention yet further includes discrete nucleotide sequences that are specific for *Neisseria gonorrhoeae,* as defined hereinabove, and that are capable of hybridizing to the deposited discrete nucleotide sequences that are specific for *Neisseria gonorrhoeae* or discrete flanking nucleotide sequences thereof that are specific for *Neisseria gonorrhoeae.* The deposited discrete nucleotide sequences that are specific for *Neisseria gonorrhoeae* and discrete flanking nucleotide sequences thereof that are specific for *Neisseria gonorrhoeae* can be utilized as a probe to rapidly screen discrete nucleotide sequences that may be specific for *Neisseria gonorrhoeae.* The discrete nucleotide sequences that hybridize to the deposited discrete nucleotide sequences that are specific for *Neisseria gonorrhoeae* or the discrete flanking nucleotide sequences thereof that are specific for *Neisseria gonorrhoeae* must be tested to determine whether or not they are specific for *Neisseria gonorrhoeae.*

Yet also included within the subject invention are discrete flanking nucleotide sequences that are specific for *Neisseria gonorrhoeae* of the discrete nucleotide sequences that are specific for *Neisseria gonorrhoeae* and that are capable of hybridizing to the deposited discrete nucleotide sequences that are specific for *Neisseria gonorrhoeae* or discrete flanking nucleotide sequences thereof that are specific for *Neisseria gonorrhoeae.* These flanking nucleotide sequences are the discrete nucleotide sequences directly adjacent on the chromosomal DNA of the discrete nucleotide sequences that are specific for *Neisseria gonorrhoeae* that are capable of hybridizing to the deposited discrete nucleotide sequences that are specific for *Neisseria gonorrhoeae* or discrete flanking nucleotide sequences thereof that are specific for *Neisseria gonorrhoeae.* These discrete flanking nucleotide sequences can be obtained by the procedure outlined in Example I.

Also included within the subject invention are discrete subsequences that are specific for *Neisseria gonorrhoeae* of the discrete nucleotide sequences that are specific for *Neisseria gonorrhoeae* and discrete flanking nucleotide sequences thereof that are specific for *Neisse-*

*ria gonorrhoeae* and that are capable of hybridizing to he deposited discrete nucleotide sequences that are specific for *Neisseria gonorrhoeae* or discrete flanking nucleotide sequences thereof that are specific for *Neisseria gonorrhoeae*.

Also included within the subject invention are discrete nucleotide sequences that are specific for *Neisseria gonorrhoeae* and that are derived from mutational changes of: (1). the discrete nucleotide sequences that are specific for *Neisseria gonorrhoeae* that are capable of hybridizing to the deposited discrete nucleotide sequences that are specific for *Neisseria gnorrhoeae* or discrete flanking nucleotide sequences thereof that are specific for *Neisseria gonorrhoeae*, (2). discrete flanking nucleotide sequences of (1). that are specific for *Neisseria gonorrhoeae* and (3). discrete nucleotide subsequences of (1). and (2). that are specific for *Neisseria gonorrhoeae*.

The screening procedure described hereinabove can be utilized to identify discrete nucleotide sequences that are specific for *Neisseria gonorrhoeae* other than those that are deposited at the ATCC. Such other discrete nucleotide sequences are within the scope of the subject invention. Such other discrete nucleotide sequences can be identified by varying one or more of the following parameters:

1. One can screen more recombinant bacteriophage molecules. The more recombinant bacteriophage molecules one screens, the more likely one can identify a discrete nucleotide sequence that is specific for *Neisseria gonorrhoeae*.

2. One can use restriction enzymes other than MboI that can digest the *Neisseria gonorrhoeae* genome. Different restriction enzymes will result in different *Neisseria gonorrhoeae* DNA fragments. Even further, one can digest the *Neisseria gonorrhoeae* genome with more than one restriction enzyme. This will provide smaller DNA fragments of the *Neisseria gonorrhoeae* genome and therefore, such DNA fragments will be less likely to hybridize to the DNA of a strain of *Neisseria meningitidis.*

3. Rather than digesting the *Neisseria gonorrhoeae* DNA with a restriction enzyme, one can break the genome into fragments by random shearing of the genome by, for example, sonication. This can provide *Neisseria gonorrhoeae* DNA fragments that would not otherwise be provided by digestion with a restriction enzyme and yet is a discrete nucleotide sequence that is specific for *Neisseria gonorrhoeae.*

4. One can vary the strain of *Neisseria gonorrhoeae* that is utilized to make the *Neisseria gonorrhoeae* DNA fragments.

Also, it is essential to note that any composition that fulfills the requirements of the compositions of the subject invention is within the scope of the subject invention, regardless of how such compositions are obtained. That is to say, even if the composition is obtained by a method other than the screening procedure described hereinabove, it is covered by the subject invention.

The test described in step "H" that determines whether or not a composition is covered by the subject invention should be slightly modified if the composition consists essentially of discrete oligonucleotide sequences; i.e., discrete nucleotide sequences of fewer than about 50 base pairs. It is essential to change the hybridization and wash temperature for discrete oligonucleotide sequences. At 65° C. an oligonculeotide sequence may remain largely unhybridized after the hybridization reaction. The temperature at which the hybridization and wash should be carried out is Tm(°C.)− +° C. of the composition containing the discrete oligonucleotide sequences wherein such determination is made in a solution having a salt concentration of 2X, SSC, wherein Tm is the denaturation temperature of the discrete oligonucleotide sequences. The Tm of the composition can be calculated or determined by standard techniques. If the discrete oligonucleotide sequences is made synthetically, then such oligomers complementary sequence must be synthesized to determine the Tm. Also, it should be noted that for the purpose of the subject invention a discrete oligonucleotide sequence which has a non-*Neisseria gonorrhoeae* polynucleotide tail attached thereto, eg, poly A, should be considered a discrete oligonucleotide sequence.

It is essential to note that the compositions of the subject invention can comprise one discrete nucleotide sequence or of many discrete nucleotide sequences. Thus, when the compositions of the subject invention comprise many discrete nucleotide sequences, each discrete nucleotide sequence may not be specific for *Neisseria gonorrhoeae,* but the composition is specific for *Neisseria gonorrhoeae.* This is due to the fact that each discrete nucleotide sequence can not hybridize to the *Neisseria meningitidis* DNA of any of the six strains of *Neisseria meningitidis* and can not hybridize to the *Neisseria gonorrhoeae* DNA of all of the six strains of *Neisseria gonorrhoeae.* Compositions of the subject invention that comprise many discrete nucleotide sequences can be obtained by either a mixture of discrete nucleotide sequences derived from ore than one recombinant bacteriophage DNA or one recombinant bacteriophage DNA wherein the nucleotide sequence insert is chopped into many discrete nucleotide sequences, for example, as a consequence of nick translation.

Compositions of the subject invention derived from more than one recombinant bacteriophage DNA can be obtained in step G wherein those recombinant bacteriphage DNA that give a ratio of the strain of *Neisseria gonorrhoeae* that gave the greatest number of counts per minute compared with the strain of *Neisseria meningitidis* that gave the greatest number of counts per minute greater than about five can also be utilized in the procedure of step H. Thus, these recombinant bacteriophage DNA are capable of identifying at least one, but not all, of the strains of *Neisseria gonorrhoeae.* They may be able to be utilized in combination with other recombinant bacteriophage DNA that also give such a ratio greater than about five wherein such a "cocktail" results in a composition of the subject invention.

METHOD FOR THE DETECTION OF NEISSERIA GONORRHOEAE

Another aspect of the subject invention is the method of use of the compositions of the subject invention in a hybridization assay for the detection of *Neisseria gonorrhoeae.* Any hydridization method known or to be developed in the future can be utilized in the subject invention. See U.S. Pat. No. 4,458,535, Falkow et al., the disclosure of which is incorporated herein by reference.

Prior to utilizing the compositions of the subject invention in a hydridization assay, such compositions should be labelled with a detectable marker, e.g. radioisotopes, enzyme. A hybridization assay generally comprises, but is not limited to, immobilizing, either the *Neisseria gonorrhoeae* sample or the compositions of the subject invention to a matrix, and treating the matrix so as to prevent non-specific binding to the matrix of the compositions of the subject invention. The labelled composition of the subjection invention then is utilized to contact the sample on the matrix under hybridizing conditions. Components not specifically hybridized to the *Neisseria gonorrhoeae* sample are removed for example, by washing the matrix. The lable of the composition is then detected and if the label is present, *Neisseria gonorrhoeae* is present.

METHOD FOR THE DETECTION OF A GENETICALLY DISTINCT GROUP

In yet another aspect of the present invention is that the screening procedure described hereinabove provides a very expedient method to screen for a nucleotide sequence that is specific for a genetically distinct group, e.g. *Neisseria gonorrhoeae*.

This method comprise the following steps:

A method of screening for a nucleotide sequence that is specific for a genetically distinct group comprises:

a. forming a separate test dot on a matrix for each sample that said nucleotide sequence is to be screened against wherein each test dot comprises purified DNA in single stranded form from one of said samples;

b. contacting said test dots with said nucleotide sequence wherein said nucleotide sequence is a single stranded nucleotide sequence insert in a bacteriophage DNA wherein said bacteriophage is a bacteriophage that has a single stranded DNA stage in its life cycle, under hybridizing conditions;

c. separating said nucleotide sequence that did not hybridize to said test dots from said nucleotide sequence that did hybridize to said test dots;

d. contacting said test dots with denatured double stranded DNA of said bacteriophage wherein said denatured double-stranded DNA of said bacteriophage has a detectable marker attached thereto, under hybridizing conditions;

e. separating said labeled double stranded DNA of said bacteriophage that did hyridize to said test dots from said double stranded DNA of said bacteriophage that did not hybridize to said test dots; and f. detecting said nucleotide sequence by means of said detectable marker.

The following examples are offered by way of illustration and not by way of limitation.

EXAMPLE I

Procedure for the identification and isolation of the flanking nucleotide sequences of the *Nesseria gonorrhoeae* insert of ATCC 53409, ATCC 53410 and ATCC 53411. (This is commonly referred to as "chromosomal walking" in the scientific literature.)

This procedure is carried out by isolating clones containing the flanking nucleotide sequences of the *Neisseria gonorrhoeae* insert of each of ATCC 53409, ATCC 53410 and ATCC 53411, and then investigating the specificity of these sequences in terms of their reactivity with *Nesseria gonorrhoeae* and *Neisseria meningitidis* DNA. This procedure will also reveal the size of those discrete flanking nucleotide sequences that are specific for *Neisseria gonorrhoeae.*

(A) Cloning

The size of the discrete nucleotide sequence insert of ATCC 53409, ATCC 53410 and ATCC 53411, ranges from about 0.85 to about 1.3 kb. In order to find larger segments of *Neisseria gonorrhoeae* DNA that contain the flanking nucleotide sequences of ATCC 53409, ATCC 53410 and ATCC 53411 a bacteriophate lambda cloning system is used. EMBL 3 and EMBL 4 are lambda vectors with a cloning capacity of 9–23 kb. (Frischauf, A., et. al. (1983) J. Mol. Biol. 170: 827–842). First the *Neisseria gonorrhoeae* DNA from any of the six deposited strains of *Neisseria gonorrhoeae* is partially digested by Bam Hl to an average size of about 15 kb. These fragments are then used to construct a library with Bam Hl digested EMBL 3 vector. These fragments must also be dephosphorylated to insure that every lambda clone will contain only one piece of Bam cut DNA. (See Maniatis et. al.). After ligation, the DNA is packaged with the "Gigapack" packaging mixture obtained from Vector Cloning Systems (San Diego, CA (GP 10).

(B) Vitro Packaging

The "Gigapack" in vitro packaging kit obtained from Vector Cloning Systems contains sets of sonicated and freeze/thaw extracts. When ready, the appropriate number of sets is removed from the −80° C. freeze and place on ice. The freeze/thaw extract is rolled between the fingers until just thawed, and returned to the ice. The sonicated extract is also thawed this way. DNA is added to the freeze/thaw tube and returned to the ice. 15 ul of sonicated extrct is added to the DNA/freeze/-thaw mixture and mixed well. The reaction is incubated at 22° C. for 2 hours. Afterwards, 0.5 ml of bacteriophage dilution buffer (5.8 g NaCl, 2 g MgSO4*7H20, 50 ml 1M Tris*Cl (pH 7.5), 5 ml 2% gelatin per liter) and 20 ul chloroform (do not add chloroform to polystyrene tubes—reactions must be in polypropylene tubes) is added and mixed gently. This solution can now be treated as a bacteriophage stock. Four consecutive 10-1 dilutions in bacteriophage dilution buffer (final is a 10-5 dilution) are made and 10 ul from each tube is plated out. Plaques will appear after 12 hours of incubation at 37° C. The packaging extract will yield anywhere between $10^4$ to $10^8$ plaques for every ug of DNA added to the extract.

(C) Plating Out Recombinant Bacteriophage

The strain of *E. coli* used as the host is NM 539, a bacteriophage P1 lysogen that permits only recombinant lambda bacteriophage to infect it. A culture of the host bacteria is grown the night prior to packaging in TB medium (10 g of Bacto-tryptpne (Difco) and 5 g of NaCl per liter of deionized water with the pH adjusted to 7.4) supplemented with 10 mM $MgSO_4$ and 0.2% maltose after autoclaving. 1M $MgSO_4$ and 20% maltose stock solutions are filter-sterilized. The NM 539 culture is incubated in a 30° C. shaking waterbath at 200 rpms overnight. The lower temperature prevents the bacteria from overgrowing. The next day the bacteria are pelleted at 2000 rpm for 10 minutes and resuspended in 10 mM $MgSO_4$, at a volume of 0.4 times the original culture volume. The optical density is read at 600 nm. 0.2 ml of bacteria adjusted to an optical density of 0.5 (about 3×108 bacteria per ml) is used with sterile bacteriophage dilution buffer and 3 mls of top agarose (0.7% low EED agarose in NZY medium). The bacteriologic plates are poured with NZY agar (NZY medium plus 1.5% bacto-agar; NZY medium is 10 g NZ amine (ICN Pharm.), 5 g NaCl, 5 g yeast extract, 2 g MgSO 4*7H20 per liter adjusted to pH 7.5 with NaOH). Plates are allowed to dry overnight at room temperature and warmed to 37° C. before plating bacteriophage. The best number of plaques on each plate is about 200 to 300 plaques.

(D) Preparation of Filters

Nylon membrane filters (Pall Ultrafine Filtration Corp.) are placed upon the plates for 30 seconds. This will transfer some of the bacteriophage from the plaques to the membrane forming a "replica" of the plate. Each of the plates and membranes has been previously marked to insure that each membrane can later be matched with the appropriate plate and also so that the physical orientation of the filter on the plate can also be determined.

Each membrane is then processed further by laying onto Whatman No. 3 paper which has been saturated with 1.5M NaCl/0.5M NaOH-for 1 minute. Filters are then transferred to paper saturated with 1.5M NaCl/0.5M Tris-Cl pH 8.0 for 5 minutes, followed by transfer to 2X SSC (1X SCC=0.15M NaCl, 0.015M $Na_3$ Citrate) for 5 minutes. The filters are allowed to air dy and then baked in vacuo at 80° C. for 1 hour.

(E) Prehybridization

The baked filters are floated on the surface of 6X SSC until thoroughly wetted from underneath (about 5 minutes). The filter is then transferred to a plastic bag (such as Seal-a-Meal bag) containing 100 ml of the prewashing solution (50 mM Tris-Cl pH 8.0, 1M NaCl, 1 mM EDTA and 0.1% SDS) and incubated at 42° C. for 1–2 hour with gentle agitation. After the filter is removed and drained, it is put in the bag containing the prehybridization solution (6X, SSC, 5X Denhardt's solution, 0.1% SDS, 100 ug/ml of sonicated, heat denaturated calf thymus DNA). The prehybridization is carried out for 2–4 hours at 65° C. in a shaking water bath set for 50 rpm.

(F) Hybridization

DNA from ATCC 53409, ATCC 53410 or ATCC 53411 is labeled with $^{32}P$ by means of nick translation and utilized as a probe. When ready for use, the probe is denatured by immersing a tube containing the probe into boiling $H_2O$ for 5 minutes followed by quenching into ice/$H_2O$. After prehybridization, the prehybridization solution is squeezed out and replaced with the hybridization solution (prehybridization solution plus 100 ug/ml of yeast tRNA and heat denaturated $^{32}P$ labeled probe as described hereinabove). The hybridization is carried out at 65° C. in the water bath with gentle shaking for 40 to 48 hours.

(G) Washing

After hybridization, membranes are removed from plastic bags and placed in a plastic box. The membranes are then washed with gentle shaking at 65° C.; three times with 2X SSC, 0.1% SDS for 30 minutes each.

(H) Autoradiography

The washed membranes are air dried and exposed to Kodak XRP-5 x-ray film. Those plaques which hybridized with probe will give rise to black spots on the film.

(I) Verifying Plaques

Those plaques which have been identified as candidates by the ability to hybridize with the probe are then picked and rechecked by stabbing from each plaque onto NZY agar plates with an overlayer of TLA containing fresh host bacteria. The procedure is repeated from (C) to (H).

(J) Bacteriophage Stocks

Those plaques which have been positively identified as possessing discrete nucleotide sequences homologous to ATCC 53409, ATCC 53410 or ATCC 53411 are used to grow up stocks by stabbing from the plaque into freshly growing host bacteria. These stocks can be expanded as necessary.

(K) Results of Steps A Through J

At this point, plaques have been selected on the basis of homology with the *Neisseria gonorrhoeae* insert of ATCC 53409, ATCC 53410 or ATCC 53411. They will therefore have large streches of DNA derived from *Neisseria gonorrhoeae* which will contain all or part of the *Neisseria gonorrhoeae* insert of ATCC 53409, ATCC 53410 or ATCC 53411.

(L) Preparation of DNA from Phage Stocks 1.5 ml of phage stock is digested with 10 ug/ml Deoxyribonuclease I (Sigma Chemical Co.) in the presence of 10 mM $MgSO_4$ for 1 hour at 25°–30° C. (room temperature). This step digests any chromosomal DNA present in the bacteriophage stock after lysis of host cells while the DNA that is inside the bacteriophage particles is protected by the bacteriophage coat proteins. An equal volume of phenol equilibrated with TE buffer (10 mM Tris-Cl pH=8.0, 1 mM EDTA) is then added to the bacteriophage solution and shaken vigorously). Centrifugation at 9,000 rpm in a savant high speed centrifuge (or its equivalent) for 5 minutes results in the separation of two phases with protein at the interface. The top layer (aqueous) containing the DNA is carefully taken off and the DNA is precipitated by the addition of 1/10th volume of 3M NaOAc and 2 volumes of 95% ETOH followed by cooling in a dry ice/ETOH bath. The supernatant is removed by centrifugation at 9,000 rpm for 10 minutes followed by a quick rinse with a solution of 70% ETOH/30% $H_2O$. The pellet is then dried in a lyophilizer and resuspended in 0.1 ml of TE buffer.

(M) Restriction Enzyme Mapping 5 ul aliquots are then digested with various restriction enzymes either singly or in combination, and the resultant fragments separated out by gel electrophoresis on 0.7% to 2.0% agarose gels in TBE buffer (0.089M Tris-borate, 0.089M boric acid, 0.002M EDTA). Gels are stained by immersion in 5 mg/ml ethidium bromide followed by illumination by ultra-violet light at 240–320 nM wavelength. At this point it should be determined whether there is enough DNA to visualize all the digestion products (or too much) and whether digestion was complete. Adjustments can be made in subsequent digestions by changing the amount of DNA and/or restriction enzyme. Analysis of the various products of these digestions will result in alinear map of the locations of restriction enzyme sites on each of the clones. From this type of analysis, areas of overlap between the various clones can be established. This also allows the choice of which enzyme or enzymes should be used for subcloning. A southern blot can be made of the gel containing the various restriction enzyme digests and the location of the inserts from ATCC 53409, 53410 or 53411 can be pinpointed on the restriction enzyme map. At this point one can choose the restriction enzymes that cut immediately adjacent to these inserts so that the sequences directly adjacent to the insert, which are the flanking nucleotide sequences, can be subcloned and tested for specificity.

(N) Subcloning Fragments

Stocks of bacteriophage should be expanded and DNA prepared (as described in part K) so that an adequate supply of DNA for each clone can be obtained. The DNA is digested with the appropriate enzyme(s) as determined in the previous step and a vector with the corresponding site(s) is also digested. An appropriate vector for this step would be determined by the choice of restriction enzyme(s) used for subcloning. One vector that might be useful would be pIBI 76 since it has a "polylinker" which is an artificially constructed array of many commonly used restriction sites. The vector is also designed such that after transformation with a ligation mixture of vector and insert DNA, clones can be selected for the presence of vector by resistance to ampicillin and also for the presence of an insert in the vector by the blue vs. white phenotype as previously described hereinabove for M13 clones, with the difference that in this case one will be looking for white colonies instead of white plaques. Clones can then be picked, grown up and plasmid DNA isolated using standard procedures described by Maniatis. Clones can then be nick-translated with $^{32}P$ label and identification of clones that are specific for *Neisseria gonorrhoeae* can be performed as described hereinabove in step H. If clones of DNA derived from nucleotide sequences that are flanking nucleotide sequences of *Neisseria gonorrhoeae* inserts from ATCC 53409, 53410 or 53411 prove to be specific for *Neisseria gonorrhoeae*, as defined hereinabove, the nucleotide sequences directly adjacent to these flanking nucleotide sequences can also be cloned and tested for specificity. This can be repeated by picking clones that are farther and farther away from the original inserts until they are no longer specific for *Neisseria gonorrhoeae*, and all nucleotide sequences beyond that point on the genome are mot flanking nucleotide sequences and thus, are not within the scope of the subject invention. The DNA inserts of each of the clones that are specific for *Neisseria gonorrhoeae* define the discrete flanking nucleotide sequences on each side of ATCC 534409, ATCC 53410 and ATCC 53411 and thus, are within the scope of the subject invention.

EXAMPLE II

This example determines whether or not a discrete nucleotide sequence is a composition of the subject invention.

Preparation of the Test Dots

The following six strains of *Neisseria meningitidis* and six strains of *Neisseria gonorrhoeae*, having the following ATCC accession numbers, were utilized for the preparation of the test dots.

| *Neisseria meningitidis* | *Neisseria gonorrhoeae* |
|---|---|
| 1. 53414 | 1. 53420 |
| 2. 53415 | 2. 53421 |
| 3. 53416 | 3. 53422 |
| 4. 53417 | 4. 53423 |
| 5. 53418 | 5. 53424 |
| 6. 53419 | 6. 53425 |

The ATCC supplies the samples of the above strains in a lypholized state. Each of the twelve strains was grown on 4-6 plates of chocolate agar plate by streaking the culture with a cotton swab. After incubation overnight in a $CO_2$ incubator (10% $CO_2$), the cells were harvested by collecting onto a cotton swab and resuspended with TE buffer (10 mM Tric-Cl pH 8.0, 1 mM EDTA) and resuspended in TE buffer. For each plate, 1 ml of TE buffer was used. Chromosomal DNA of Niesseria was isolated by lysing the cells with SDS (0.1% final concentration). The DNA was sheared by passage through gauge a 22 syringe needle 3-4 times, followed by RNase digestion (10 ug/ml final concentration incubation for 30 minutes at room temperature) and phenol extraction (three times with TE saturated phenol). Sodium Acetate (ph=7.4 was added to a final concentration of 0.3M and then two volumes of 95% ethanol was added. The chromosomal DNA was then collected with a pasteur pipett by spooling out the precipitated DNA from the ethanol solution. The DNA fiber was transferred to a test tube and washed two times with 75% ethanol (25% TE buffer). The remaining ethanol was removed by placing the tube in a speed-vac centrifuge and run under vacuum for a few minutes. The DNA was then dissolved by adding a small volume of TE buffer (about 1 ml for 6 plates of culture) and allowed to stand at 4° C. with occasional gentle shaking overnight. Purity of DNA was checked by agarose gel electrophoresis and by comparing the ratio of optical densities at 260 nm and 280 nm. (A good preparation of DNA should have a ratio above 1.8). The purified chromosomal DNA was then denatured with 0.2N NaOH (final concentration) for 10 minutes at room temperature and the pH was adjusted to about 7.8 by adding $NH_4A_c$ which resulted in a final concentration of 1M $NH_4A_c - 0.02N$ NaOH.

For each of the twelve denatured purified chromosomal DNAs, six tests dots were prepared. Each of the six dots was serially diluted by a factor 10 with 1M $NH_4OAc$ such that the six tests dots contained the following amounts of the denatured purified choromosomal DNA: 500 nanograms, 50 nanograms, 5 nanograms, 0.5 nanograms, 50 picograms and 5 picograms. Accordingly, there were six test dots for each strain, resulting in a total of 72 test dots.

Preparation of Test DNA Dots 100-200 ul of 1M $NH_4OAc$ containing the appropriate amount of DNA was applied to nitrocellulose membranes with a dot blot apparatus with a 36 sample manifold under a vacuum of 10 inch Hg. Each sample was washed with 1M $NH_4OAc$ and 4X SSC. The nitrocellulose membrane was then air dried and baked under vacuo for 1 hour at 80° C. in a vacuum oven. These nitrocellulose membrane can be stored in air tight plastic bags with a drying agent for as long as one month before use.

Hybridization to the Test Dot

The RF DNA of each of the recombinant DNA molecule of ATCC 53409, ATCC 53410 and ATCC 53411 was isolated from its *E. Coli* host. Each contains a recombinant DNA molecule consisting of a piece of *Neisseria gonorrhoeae* DNA inserted into a vector derived from M13 bacteriophage. These recombinant DNA molcule are then isolated as RF form from bacteria using a standard plasmid DNA preparation procedures (see Maniatis).

The RF DNA was then $^{32}$P labelled by nick translation using by standard techniques (see Maniatis) such that the specific activity of $^{32}$P labelling was from $10^7$–$10^8$ cpm/ug of DNA.

The $^{32}$P labelled RF DNA was then utilized to hybridize to the test dots as follows:

Before hybridization, the nitrocellulose membrane was put in a plastic bag (such as seal-a-meal bag) containing 2X SSC, 5X Denhardt's solution, 0.1% SDS, 100 ug/ml of sonicated denaturated calf thymus DNA and incubated at 65° C. for 2 hours with gentle shaking. The prehybridization step is used to block any possible non-specific binding sites either located on the matrix or on the nitrocellulose membrane or on the test DNA dots.

The $^{32}$P labelled RF DNA was denatured by boiling it in water bath for 10 minutes. The denatured $^{32}$P labelled RF DNA was quick cooled in ice-water, then added to a hybridization solution consisting of 2X SSC, 5X Denhardt's solution 0.1% SDS, and 100 micrograms/ml. of sonicated heat denatured calf thymus DNA and 100 micrograms/ml of yeast +t RNA. This mixture was then placed in a plastic bag with one or several nitrocellulose filters, each containing the test dots for about 40 hours at 65° C. with gentle shaking. After hybridization, the nitrocellulose membranes were removed from their bags and washed twice for about 30 minutes each in prewarmed 2X SSC, 0.1% SDS followed by two more 30 minutes washes prewarmed in 0.2 X SSC, 0.1% SDS, with all four washes being carried out at 65° C. with gentle shaking during each of the four washes. The mixture was then air dried.

The Quantification of the Radioactivity of the $^{32}$P of the Hybrid

The nitrocellulose filter was then exposed to X-ray film. The developed X-ray film was then used as a reference marker by placing it over the filter to permit each test dot to be cut from the filter and placed in a vial containing scintillation fluid. Each of the vials was then placed in the scintillation counter and the radioactivity of the $^{32}$P of the hybrid was quantified, albeit the radioactivity of the $^{32}$P wherein the amount of denatured purified chromosomal DNA on the test dot was 0.5 nanograms, 50 picograms and 5 picograms was not quantified because the number of counts/minute at 0.5 nanograms would have resulted in fewer counts/minute than that of the matrix background. The results, as stated in counts per minute and after subtracting matrix background, were as follows:

TABLE I

ATCC 53409
COUNTS/MINUTE AFTER SUBTRACTING MATRIX BACKGROUND

| Strain of | Amount of Denatured Purified Chromosomal DNA on Test Dot | | |
|---|---|---|---|
| | 500 ng. | 50 ng. | 5 ng. |
| Niesseria gonorrhoeae | | | |
| ATCC 53420 | .3775 | 387 | 33 |
| ATCC 53421 | 20699 | 2362 | 271 |
| ATCC 53422 | 4349 | 446 | 63 |
| ATCC 53423 | 19010 | 2455 | 304 |
| ATCC 53424 | 15942 | 1727 | 181 |
| ATCC 53425 | 19479 | 2149 | 217 |
| Neisseria meningitidis | | | |
| ATCC 53414 | 0 | 0 | 0 |
| ATCC 53415 | 0 | 0 | 6 |
| ATCC 53416 | 0 | 0 | 0 |
| ATCC 53417 | 0 | 0 | 0 |

TABLE I-continued

| ATCC 53418 | 0 | 0 | 0 |
| ATCC 53419 | 0 | 0 | 63 |

ATCC 53410
COUNTS/MINUTE AFTER SUBTRACTING MATRIX BACKGROUND

| Strain of | Amount of Denatured Purified Chromosomal DNA on Test Dot | | |
|---|---|---|---|
| | 500 ng. | 50 ng. | 5 ng. |
| Neisseria gonorrhoeae | | | |
| ATCC 53420 | 509 | 51 | 0 |
| ATCC 53421 | 7190 | 854 | 54 |
| ATCC 53422 | 9318 | 1631 | 105 |
| ATCC 53423 | 802 | 27 | 0 |
| ATCC 53424 | 833 | 70 | 0 |
| ATCC 53425 | 2296 | 212 | 0 |
| Neisseria meningitidis | | | |
| ATCC 53414 | 56 | 0 | 0 |
| ATCC 53415 | 26 | 0 | 0 |
| ATCC 53416 | 0 | 0 | 0 |
| ATCC 53417 | 0 | 0 | 0 |
| ATCC 53418 | 0 | 0 | 0 |
| ATCC 53419 | 0 | 0 | 0 |

ATCC 53411
COUNTS/MINUTE AFTER SUBTRACTING MATRIX BACKGROUND

| Strain of | Amount of Denatured Purified Chromosomal DNA on Test Dot | | |
|---|---|---|---|
| | 500 ng. | 50 ng. | 5 ng. |
| Neisseria gonorrhoeae | | | |
| ATCC 53420 | 911 | 133 | 0 |
| ATCC 53421 | 7964 | 988 | 108 |
| ATCC 53422 | 9125 | 2592 | 256 |
| ATCC 53423 | 2617 | 325 | 0 |
| ATCC 53424 | 1448 | 130 | 0 |
| ATCC 53425 | 4204 | 521 | — |
| Neisseria meningitidis | | | |
| ATCC 53414 | 0 | 0 | 0 |
| ATCC 53415 | 6 | 0 | 0 |
| ATCC 53416 | 0 | 0 | 0 |
| ATCC 53417 | 0 | 0 | 0 |
| ATCC 53418 | 0 | 0 | 0 |
| ATCC 53419 | 0 | 4 | 0 |

The number of counts/minute with 500 nanograms of purified chromosomal DNA of the test dots, i.e. the amount of Neisseria gonorrhoeae DNA hybridized to the test dots normalized to equal amounts (500 nanograms) of purified chromosomal DNA of the test dot, was then calculated for ATCC 53409, ATCC 53410 and ATCC 53411:

TABLE II

ATCC 53409
AMOUNT OF NEISSERIA GONORRHOEAE DNA HYBRIDIZED TO THE TEST DOT NORMALIZED TO EQUAL AMOUNTS (500 NANOGRAMS) OF PURIFIED CHROMOSOMAL DNA OF THE TEST DOT (COUNTS/MINUTE)

| Strain of | Amount of Denatured Purified Chromosomal DNA of Test Dot | | |
|---|---|---|---|
| | 500 ng. | 50 ng. | 5 ng. |
| Neisseria gonorrhoeae | | | |
| ATCC 53420 | 3775 | 3870 | 3300 |
| ATCC 53421 | 20699 | 23620 | 27100 |
| ATCC 53422 | 4349 | 4460 | 6300 |
| ATCC 53423 | 19010 | 24550 | 30400 |
| ATCC 53424 | 15942 | 17270 | 18100 |
| ATCC 53425 | 19479 | 21490 | 21700 |
| Neisseria meningitidis | | | |
| ATCC 53414 | 0 | 0 | 0 |
| ATCC 53415 | 0 | 0 | 600 |
| ATCC 53416 | 0 | 0 | 0 |
| ATCC 53417 | 0 | 0 | 0 |

TABLE II-continued

| | | | |
|---|---|---|---|
| ATCC 53418 | 0 | 0 | 0 |
| ATCC 53419 | 0 | 0 | 6300 |

ATCC 53410
AMOUNT OF *NEISSERIA GONORRHOEAE* DNA HYBRIDIZED TO THE TEST DOT NORMALIZED TO EQUAL AMOUNTS (500 NANOGRAMS) OF PURIFIED CHROMOSOMAL DNA OF THE TEST DOT (COUNTS/MINUTE)

| | Amount of Denatured Purified Chromosomal DNA on Test Dot | | |
|---|---|---|---|
| Strain of | 500 ng. | 50 ng. | 5 ng. |
| *Neisseria gonorrhoeae* | | | |
| ATCC 53420 | 509 | 510 | 0 |
| ATCC 53421 | 7190 | 8540 | 5400 |
| ATCC 53422 | 9318 | 16310 | 10500 |
| ATCC 53423 | 802 | 270 | 0 |
| ATCC 53424 | 833 | 700 | 0 |
| ATCC 53425 | 2296 | 2120 | 0 |
| *Neisseria meningitidis* | | | |
| ATCC 53414 | 56 | 0 | 0 |
| ATCC 53415 | 26 | 0 | 0 |
| ATCC 53416 | 0 | 0 | 0 |
| ATCC 53417 | 0 | 0 | 0 |
| ATCC 53418 | 0 | 0 | 0 |
| ATCC 53419 | 0 | 0 | 0 |

ATCC 53411
AMOUNT OF *NEISSERIA GONORRHOEAE* DNA HYBRIDIZED TO THE TEST DOT NORMALIZED TO EQUAL AMOUNTS (500 NANOGRAMS) OF PURIFIED CHROMOSOMAL DNA OF THE TEST DOT (COUNTS/MINUTE)

| | Amount of Denatured Purified Chromosomal DNA to Test Dot | | |
|---|---|---|---|
| Strain of | 500 ng. | 50 ng. | 5 ng. |
| *Neisseria gonorrhoeae* | | | |
| ATCC 53420 | 911 | 1330 | 0 |
| ATCC 53421 | 7964 | 9880 | 10800 |
| ATCC 53422 | 9125 | 25920 | 25600 |
| ATCC 53423 | 2617 | 3250 | 0 |
| ATCC 53424 | 1448 | 1300 | 0 |
| ATCC 53425 | 4204 | 5210 | — |
| *Neisseria meningitidis* | | | |
| ATCC 33414 | 0 | 0 | 0 |
| ATCC 53415 | 6 | 0 | 0 |
| ATCC 53416 | 0 | 0 | 0 |
| ATCC 53417 | 0 | 0 | 0 |
| ATCC 53418 | 0 | 0 | 0 |
| ATCC 53419 | 0 | 40 | 0 |

The average amount of *Neisseria gonorrhoeae* DNA hybridized to the dots normalized to equal amounts (500 nanograms) of purified chromosomal DNA of the test dot was then calculated by utilizing the data of Table II and for each of the six test dots of each of the strains of *Neisseria gonorrhoeae* and *Neisseria meningitidis* that are: (1). most nearly the same, and (2). the amount of purified chromosomal DNA of the test dots differs by a factor of ten, calculate their average. The results were as follows:

TABLE III

ATCC 53409
AVERAGE AMOUNT OF *NEISSERIA GONORRHOEAE* DNA HYBRIDIZED TO THE TEST DOT NORMALIZED TO EQUAL AMOUNTS (500 NANOGRAMS) OF PURIFIED CHROMOSOMAL DNA OF THE TEST DOT (COUNTS/MINUTE)

| Strain of *Neisseria gonorrhoeae* | |
|---|---|
| ATCC 53420 | 3822 |
| ATCC 53421 | 22160 |
| ATCC 53422 | 4405 |
| ATCC 53423 | 21780 |
| ATCC 53424 | 17685 |
| ATCC 53425 | 21595 |
| Strain of *Neisseria meningitidis* | |
| ATCC 53414 | 0 |
| ATCC 53415 | 0 |
| ATCC 53416 | 0 |
| ATCC 53417 | 0 |
| ATCC 53418 | 0 |
| ATCC 53419 | 0 |

ATCC 53410
AVERAGE AMOUNT OF *NEISSERIA GONORRHOEAE* DNA HYBRIDIZED TO THE TEST DOT NORMALIZED TO EQUAL AMOUNTS (500 NANOGRAMS) OF PURIFIED CHROMOSOMAL DNA OF THE TEST DOT (COUNTS/MINUTE)

| Strain of *Neisseria gonorrhoeae* | |
|---|---|
| ATCC 53420 | 510 |
| ATCC 53421 | 7865 |
| ATCC 53422 | 13405 |
| ATCC 53423 | 135 |
| ATCC 53424 | 767 |
| ATCC 53425 | 2208 |
| Strain of *Neisseria meningitidis* | |
| ATCC 53414 | 0 |
| ATCC 53415 | 0 |
| ATCC 53416 | 0 |
| ATCC 53417 | 0 |
| ATCC 53418 | 0 |
| ATCC 53419 | 0 |

ATCC 53411
AVERAGE AMOUNT OF *NEISSERIA GONORRHOEAE* DNA HYBRIDIZED TO THE TEST DOT NORMALIZED TO EQUAL AMOUNTS (500 NANOGRAMS) OF PURIFIED CHROMOSOMAL DNA OF THE TEST DOT (COUNTS/MINUTE)

| Strain of *Neisseria gonorrhoeae* | |
|---|---|
| ATCC 53420 | 1121 |
| ATCC 53421 | 10340 |
| ATCC 53422 | 25760 |
| ATCC 53423 | 2934 |
| ATCC 53424 | 1374 |
| ATCC 53425 | 4707 |
| Strain of *Neisseria meningitidis* | |
| ATCC 53414 | 0 |
| ATCC 53415 | 0 |
| ATCC 53416 | 0 |
| ATCC 53417 | 0 |
| ATCC 53418 | 0 |
| ATCC 53419 | 20 |

The lowest number of counts/minute of the data of Table III for *Neisseria gonorrhoeae* for ATCC 53409, ATCC 53410 and ATCC 53411 and the highest number of counts/minute of Table III for *Neisseria meningitidis* for ATCC 53409, ATCC 53410 and ATCC 53411 was then calculated. The results were as follows:

TABLE IV

LOWEST OF THE AVERAGE AMOUNT OF *NEISSERIA GONORRHOEAE* HYBRIDIZED TO THE TEST DOT NORMALIZED TO EQUAL AMOUNTS (500 NANOGRAMS) OF PURIFIED CHROMOSOMAL DNA OF THE *NEISSERIA GONORRHOEAE* TEST DOTS (COUNTS/MINUTES)

| | |
|---|---|
| ATCC 53409 | 3822 |
| ATCC 53410 | 135 |
| ATCC 53411 | 1121 |

HIGHEST OF THE AVERAGE AMOUNT OF *NEISSERIA GONORRHOEAE* DNA HYBRIDIZED TO THE TEST DOT NORMALIZED TO EQUAL AMOUNTS

TABLE IV-continued (500 NANOGRAMS) OF PURIFIED CHROMOSOMAL DNA
OF THE *NEISSERIA MENINGITIDIS* TEST DOTS
(COUNTS/MINUTES)

| ATCC 53409 | 0 |
| ATCC 53410 | 0 |
| ATCC 53411 | 20 |

Thus, the ratio of the lowest of the average amount of *Neisseria gonorrhoeae* DNA hybridized to the purified chromosomal DNA of each of the six strains of *Neisseria gonorhoeae*, normalized to equal amounts of purified chromosomal DNA of each of the six strains of *Neisseria gonorrhoeae* and the highest average amount of *Neisseria gonorrhoeae* DNA hybridized to the purified chromosomal DNA of each of the six strains of *Neisseria meningitidis*, normalized to equal amounts of purified chromosomal DNA of each of the six strains of *Neisseria meningitidis* is:

ATCC 53409-3822:0
ATCC 53410-135:0
ATCC 53411-1121:20

Accordingly, since such ratio is greater than about five, the *Neisseria gonorrhoeae* DNA insert of ATCC 53409, ATCC 53410 and ATCC 53411 is each a composition of the subject invention.

What is claimed is:

1. A composition of matter that is specific for *Neisseria gonorrhoeae* comprising at least one nucleotide sequence for which the ratio of the amount of said sequence which hybridizes to chromosomal DNA of *Neisseria gonorrhoeae* to the amount of said sequence which hybridizes to chromosomal DNA of *Neisseria meningitidis* is greater than about five, said ratio being obtained by a method comprising the folllowing steps;
    (a) providing a radioactively labeled form of said nucleotide sequence;
    (b) providing a serial dilution series of purified chromosomal DNA from each of the *N. gonorrhoeae* strains; (1) ATCC 53420, (2) ATCC 53421, (3) ATCC 53422, (4) STCC 53423, (5) ATCC 53424, (6) ATCC 53425, and forming test dots from each of said dilution series on a matrix;
    (c) providing a serial dilution series of purified nucleotide sequences from each of the *N. meningitidis* strains: (1) ATCC 53414, (2) ATCC 53415, (3) ATCC 53416, 1 (4) ATCC 53417, (5) ATCC 53418, (6) ATCC 53419, and forming test dots from each of said dilution series on a matrix;
    (d) hybridizing equal portions of the labeled nucleotide sequences to the matrix provided in step (b) and (c), respectively; wherein the hybridization is conducted in a solution having a slat concentration of 2X SSC at (i) 65° C. in cases in which the sequence has greater than 50 base pairs or (ii) at Tm (°C.) minus 30° C. in cases in which the sequence has less than 50 base pairs, wherein Tm is the denaturation temperature of the sequence;
    (e) quantifying the labeled nucleotide sequence hybridized in step (d) to each test dot;
    (f) subtracting from the data of step (a) an averaged amount of radioactivity attributable to background to obtain a corrected amount of hybridized radioactivity at each test dot;
    (g) normalizing the data of step (f) by multiplying the amount of corrected radioactivity at each test dot by a factor which adjusts the amount of radioactivity to equal amounts of chromosomal DNA at each test dot;
    (h) selecting two normalized values that are most nearly the same and that correspond to adjacent members of the dilution series for each of the above strains of *N. gonorrhoeae* and obtaining the average of the selected values;
    (i) selecting two normalized values that are most nearly the same and that correspond to adjacent members of the dilution series for each of the above strains of *N. meningitidis* and obtaining the average of the selected values;
    (j) dividing the lowest average obtained in step (h) by the highest average obtained in step (i) to obtain said ratio.

2. The composition of claim 1 wherein said ratio is greater than about 25.

3. The composition of claim 1 wherein said ratio is greater than about 50.

4. The composition of claim 1 wherein said nucleotide sequences are selected from the group consisting of:
    a. the *Neisseria gonorroheae* DNA insert of ATCC 53409, ATCC 53410 and ATCC 53411, and discrete nucleotide subsequences thereof,
    b. mutated discrete nucleotide sequences of any of the foregoing inserts that are within said hybridization ratio and subsequences thereof; and
    c. mixtures thereof.

5. In a nucleic acid hybridization assay for the detection of *Neisseria gonorrhoeae* utilizing a polynucleotide probe, wherein said probe is contacted with a sample and the amount of any hybridized probe is detected, the improvement which comprises utilizing as said nucleotide probe a composition of claim 1, wherein said composition is labeled with a detectable marker.

6. The method of claim 5 wherein the polynucleotide probe is a composition selected from the group consisting of the *Neisseria gonorrhoeae* DNA insert of ATCC 53409, ATCC 53410 and ATCC 53411, and discrete nucleotide subsequences thereof; and mutated discrete nucleotide subsequences of any of the foregoing inserts for which the ratio of the amount of said sequence which hybridizes to chromosomal DNA or *Neisseria meningitidis* is greater than about five, said ratio being obtained by the method set forth in claim 1.

* * * * *

UNITED STATES PATENT AND TRADEMARK OFFICE
CERTIFICATE OF CORRECTION

PATENT NO. : 4,900,659
DATED : February 13, 1990
INVENTOR(S) : Andrew Lo and Huey-Lang Yang It is certified that error appears in the above-indentified patent and that said Letters Patent is hereby corrected as shown below:

In column 27, Claim 1, line 42, change "STCC" to
-- ATCC --.

In column 27, Claim 1, line 48, change "1(4)" to
-- (4) --.

In column 27, Claim 1, line 54, change "slat" to
-- salt --.

In column 27, Claim 1, line 36, change "folllowing" to
-- following --.

In column 28, Claim 1, line 5, change "(a)" to
-- (e) --.

In column 28, Claim 5, lines 44-55, change "nucleotide" to
-- polynucleotide --.

Signed and Sealed this

Twelfth Day of December, 2000

Attest:

Q. TODD DICKINSON

*Attesting Officer*  *Director of Patents and Trademarks*